United States Patent [19]

Mandal et al.

[11] Patent Number: 4,568,758

[45] Date of Patent: Feb. 4, 1986

[54] PROCESS FOR THE MANUFACTURE OF OPTICALLY ACTIVE γ-LACTONE OF (1R, CIS)-2, 2-DIMETHYL-3-HYDROXYMETHYL-CYCLOPROPANE-1-CARBOXYLIC ACID

[75] Inventors: Arun K. Mandal; Shailendra R. Bhandari; Satish W. Mahajan, all of Thane, India

[73] Assignees: Indian Explosives Limited; The Alkali and Chemical Corporation of India, both of West Bengal; Chemicals and Fibres of India Limited, Maharashtra, all of India

[21] Appl. No.: 566,652

[22] Filed: Dec. 29, 1983

[51] Int. Cl.[4] ............................................ C07D 307/93
[52] U.S. Cl. .................................................. 549/302
[58] Field of Search ....................................... 549/302

[56] References Cited

U.S. PATENT DOCUMENTS

| | | | |
|---|---|---|---|
| 4,132,717 | 1/1979 | Roman | 549/302 |
| 4,219,562 | 8/1980 | Roman | 549/302 |
| 4,281,203 | 7/1981 | Syrier et al. | 549/302 |

OTHER PUBLICATIONS

Saul Patai, The Chemistry of Ethers, Crown Ethers, Hydroxyl Groups and Their Sulfur Analogues, Part 1, John Wiley & Sons, 1980, pp. 487-490.
The Chem. of Acid Derivatives, Part 1, John Wiley & Sons, 1979, pp. 310-311, pp. 333-334.
Mitra et al., Ind. J. Chem. 20, 436-7, 1981.

Primary Examiner—Jane T. Fan
Attorney, Agent, or Firm—Ladas & Parry

[57] ABSTRACT

The optically active γ-lactone of (1R, cis)-2, 2-dimethyl-3-hydroxymethyl-cyclopropane-1-carboxylic acid, which is useful as an intermediate in the production of pyrethroid insecticides, may be made from optically active (−)car-3-en-5-one by a two stage oxidation process followed by hydrolysis of the intermediate obtained.

3 Claims, No Drawings

PROCESS FOR THE MANUFACTURE OF OPTICALLY ACTIVE γ-LACTONE OF (1R, CIS)-2, 2-DIMETHYL-3-HYDROXYMETHYL-CYCLOPROPANE-1-CARBOXYLIC ACID

BACKGROUND OF THE INVENTION

The present invention relates to a process for the manufacture of Optically Active γ-lactone of (1R,Cis)-2, 2-Dimethyl-3-hydroxymethyl Cyclopropane-1-Carboxylic Acid (hereinafter referred to as Optically active (1R, Cis)-γ-lactone or optically active γ-lactone) and more particularly to the synthesis of the optically active γ-lactone from optically active Car-3-en-5-one.

Optically inactive γ-lactone of Cis-2,2-dimethyl-3-hydroxymethyl cyclopropane carboxylic acid, having the following formula I

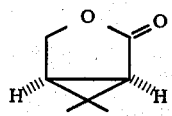

(I)

is a known compound and is manufactured by a multi-step process. Besides, this is a very well known intermediate for the manufacture of optically inactive Cis-methyl-2, 2-dimethyl-3-formyl cyclopropane carboxylate of the formula II, a valuable intermediate for the synthesis of optically inactive Cis-Chrysanthemic acid of the formula III, A-Krief et.al., Tet. Lett. 3915(1976) and Pyrethroid acid of formula IV, J. Martel et al., DOS2827627 (1979), Roussel-Uclaf. Formulae II, III and IV are shown below

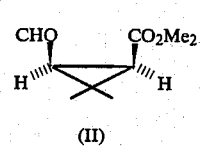

(II)

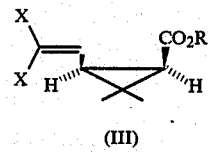

(III)

(X = CH₃ and R = H)

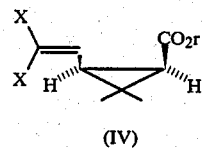

(IV)

(X = Cl, Br & R = H)

The importance of optically active γ-lactone is that it is a convenient starting material for the manufacture of optically active (1R, Cis)-Pyrethroid acid of formula IV which latter in turn could be converted to optically active (1R, Cis)-Synthetic Pyrethroid such as formula V and VI which correspond to the structure of formula III where in formula V,X=Cl and

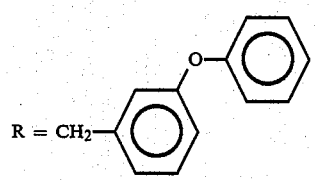

R = CH₂— and in formula VI,X=Cl or Br and

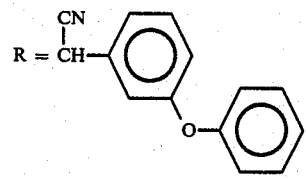

It is also established that the above optically active (1R, Cis)-Synthetic Pyrethroid possesses much more insecticidal activity than the corresponding optically inactive compounds. There is only one report available in the prior art wherein the said optically active α-lactone is synthesized from (+)-3-Carene in seven steps, see U.S. Pat. No. 4,219,562.

SUMMARY OF THE INVENTION

An object of the present invention is to produce the said optically active γ-lactone by a novel process which is short and commercially convenient.

The advantage of the present invention is apart from providing a short and commercially convenient process it excludes the use of hazardous ozonolysis reaction as is done in prior art for the manufacture of various intermediates from (+)-3-Carene useful for the manufacture of Pyrethroid insecticides.

The present invention accordingly provides a process for the manufacture of optically active γ-lactone of (1R, Cis)-2,2-dimethyl-3-hydroxymethyl cyclopropane-1-carboxylic acid which comprises the steps of oxidising optically active (−)Car-3-en-5-one of formula VII

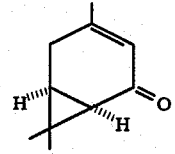

(VII)

to form optically active (−)-(1R, Cis)-2,2-dimethyl-3-(2-oxopropyl) Cyclopropane-1-carboxylic acid of formula IX,

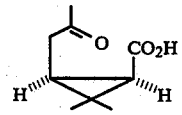

(IX)

oxidising said compound of formula (IX) to form (1R, Cis)-2,2-dimethyl-3 (acetoxymethyl)-Cyclopropane-1-Carboxylic acid of formula X

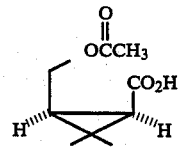

(X)

and hydrolysing the compound of formula (X) to form the optically active γ-lactone.

The compound of formula (VII) may be obtained by known methods, such as oxidation of (+)-3-carene formula VIII

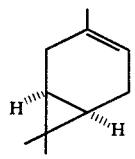
(VIII)

with air in the presence of a catalyst as described in U.S. Pat. No. 4,393,244.

The invention, thus, also provides a very short process of manufacture of the optically active compound of formula IX from (+)-3-Carene which in prior art is manufactured by multi-step processes Matsui et.al., Agric. Biol. Chem. Jap. 21, 784 (1965); R. B. Mitra et.al., Ind. J. Chem., 208, 436 (1981); (+)-(VI), W. Cocker et.al., J. C. S. Perkin I, 332 (1975).

DESCRIPTION OF THE PREFERRED EMBODIMENTS

The first step of oxidation reaction to make the intermediate compound of formula (IX) may be conducted in the liquid phase, at ambient temperature, using known oxidants, such as potassium permanganate, mixture of potassium permanganate/chromic acid, potassium permanganate—potassium dichromate (or sodium dichromate), potassium permanganate—sodium periodate and the like, in solvents such as water, acetone—acetic acid-water, or acetic acid—water mixture. The compound of formula (IX) is oxidized to the carboxylate derivative, preferably the acetate derivative of the formula (X) by the Bayer-Villegar Reaction with known oxidants such as hydrogen peroxide, per acids such as m-chloroperbenzoic acid, perbenzoic acid, perphthalic acid, peracetic acid and the like in suitable chlorinated solvents such as methylene chloride, chloroform or acetic acid at room temperature. Hydrolysis of the carboxylate of the formula (X) to the said optically active γ-lactone of formula I is conducted preferably in the same reaction zone or vessel as the said oxidation with per acids preferably under acidic condition using aqueous inorganic acids such as sulphuric acid, hydrochloric acid or the like, in polar solvents such as methanol, ethanol, dioxane, tetrahydrofuran, acetic acid or the like.

The invention is illustrated by the following examples without limiting the scope of the invention in any way. The identity of the products, including intermediates, and purity was confirmed by spectroscopic and GLC analysis as necessary.

EXAMPLE 1

(−)-(1R,Cis)-2,2-Dimethyl-3-(2.Oxopropyl)-Cyclopropane 1-Carboxylic Acid (−)-Car-3-en-5-one (15 g, 0.1 mole) was dissolved in (1:1) acetic acid-water (250 ml). To the vigorously stirred solution, solid potassium permanganate (79 g, 0.5 mole) was added portion-wise at ambient temperature. The reaction mixture was further stirred for an hour. Sulphur dioxide was passed through the reaction mixture and the residue was extracted with 3×150 ml of chloroform. The combined chloroform layer was washed with saturated brine solution (100 ml), dried over anhydrous magnesium sulphate and filtered. The solvent was stripped off under vacuum to yield 12.5 g of the product (75% yield) as a yellow viscous oil, $[\alpha]_D^{25} -30°$ (C, 0.5 CHCl$_3$)

EXAMPLE 2

γ-lactone of (−)-(1R,Cis)-Dimethyl-3-hydroxymethyl Cyclopropane-1-Carboxylic Acid To a solution of the product from example 1 (5.1 g, 0.03 mole) in dichloromethane (10 ml) was added with stirring at ambient temperature a solution of 85% m-chloroperbenzoic acid (7.2 g, 0.036 mole) in dichloromethane (20 ml). The reaction mixture was stirred for 72 h. The precipitated m-chlorobenzoic acid was filtered. The filtrate after removal of solvent was treated with methanol (10 ml) and 10% hydrochloric acid (10 ml) and stirred overnight. The reaction mixture was extracted with dichloromethane (50 ml). The organic layer was thoroughly washed with 10% aqueous sodium carbonate solution, dried over anhydrous sodium sulphate and filtered. Removal of solvent yielded γ-lactone (3.0 g, 85% yield) as a light yellow oil, $[\alpha]_D^{25} -22.5°$ (C, 0.6 CHCl$_3$).

We claim:

1. A process for the manufacture of optically active γ-lactone of (1R, Cis)-2,2-dimethyl-3-hydroxymethyl cyclopropane-1-carboxylic acid which comprises the steps of oxidising optically active (−)Car-3-en-5-one of formula VII,

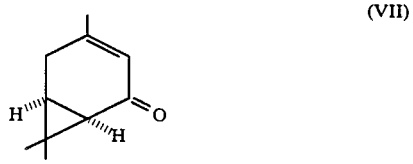
(VII)

with oxidants such as potassium permanganate, a mixture of potassium permanganate and chromic acid, potassium permanganate—potassium dichromate or sodium dichromate, or potassium permanganate—sodium periodate, in solvents such as water, acetone—acetic acid-water, or acetic acid—water mixture to form optically active (−)-(1R, Cis)-2,2-dimethyl-3-(2-oxopropyl)-cyclopropane-1-carboxylic acid of formula IX,

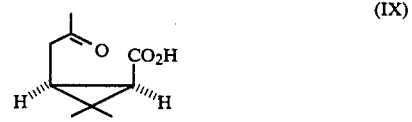
(IX)

oxidising said compound of formula (IX) by the Bayer-Villegar Reaction to form (1R, Cis)-2,2-dimethyl-3-(acetoxymethyl)-cyclopropane-1-carboxylic acid of formula X

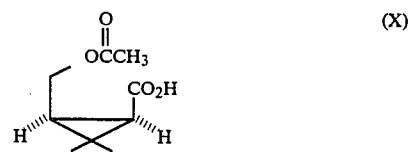
(X)

and hydrolysing the compound of formula (X) to form the optically active γ-lactone.

2. A process as claimed in claim 1 wherein the oxidation of the compound of formula IX is carried out with oxidising agents such as hydrogen peroxides, peracids such as m-chloroperbenzoic acid, perbenzoic acid, perphthalic acid, peracetic acid in the presence of a solvent like methylene dichloride, chloroform or acetic acid at room temperature.

3. A process as claimed in claim 1 wherein the hydrolysis of the intermediate (1R, Cis)-2,2-dimethyl-3-(acetoxymethyl)-cyclopropane-1-carboxylic acid of Formula X is conducted in the same reaction zone as the preceding Bayer-Villegar oxidation without isolating the said intermediate.

* * * * *